(12) United States Patent
Bayer et al.

(10) Patent No.: US 10,407,675 B2
(45) Date of Patent: Sep. 10, 2019

(54) METHOD OF FERMENTING MYCELIUM COMPOSITE MATERIAL

(71) Applicants: Eben Bayer, Troy, NY (US); Peter Mueller, Green Island, NY (US); Christopher Scully, Troy, NY (US)

(72) Inventors: Eben Bayer, Troy, NY (US); Peter Mueller, Green Island, NY (US); Christopher Scully, Troy, NY (US)

(73) Assignee: Ecovative Design LLC, Green Island, NY (US)

( * ) Notice: Subject to any disclaimer, the term of this patent is extended or adjusted under 35 U.S.C. 154(b) by 0 days.

(21) Appl. No.: 15/450,198

(22) Filed: Mar. 6, 2017

(65) Prior Publication Data
US 2017/0253852 A1  Sep. 7, 2017

Related U.S. Application Data

(60) Provisional application No. 62/304,448, filed on Mar. 7, 2016.

(51) Int. Cl.
| | | |
|---|---|---|
| *C12N 11/14* | (2006.01) | |
| *A01G 18/00* | (2018.01) | |
| *B32B 5/16* | (2006.01) | |
| *B32B 5/14* | (2006.01) | |
| *C12N 1/14* | (2006.01) | |

(52) U.S. Cl.
CPC ............. *C12N 11/14* (2013.01); *A01G 18/00* (2018.02); *B32B 5/14* (2013.01); *B32B 5/16* (2013.01); *C12N 1/14* (2013.01)

(58) Field of Classification Search
CPC .......... C12N 11/14; C12N 1/14; A01G 18/00; B32B 5/14; B32B 5/16
See application file for complete search history.

(56) References Cited

U.S. PATENT DOCUMENTS

2015/0038619 A1\*  2/2015  McIntyre ............... B27N 3/002
                                                524/13

\* cited by examiner

*Primary Examiner* — Taeyoon Kim
(74) *Attorney, Agent, or Firm* — Francis C. Hand; Carella, Byrne et al

(57) ABSTRACT

A method of fermenting mycelium composite materials wherein layers of fermentable material are stacked in alteration with ventilation layers with air being passed through the ventilation layers to remove heat and gas generated in the layers of fermentable material during fermentation thereof. The obtained composite materials may be formed into cohesive flat boards, such as are used in the manufacture of insulation or furniture.

11 Claims, 1 Drawing Sheet

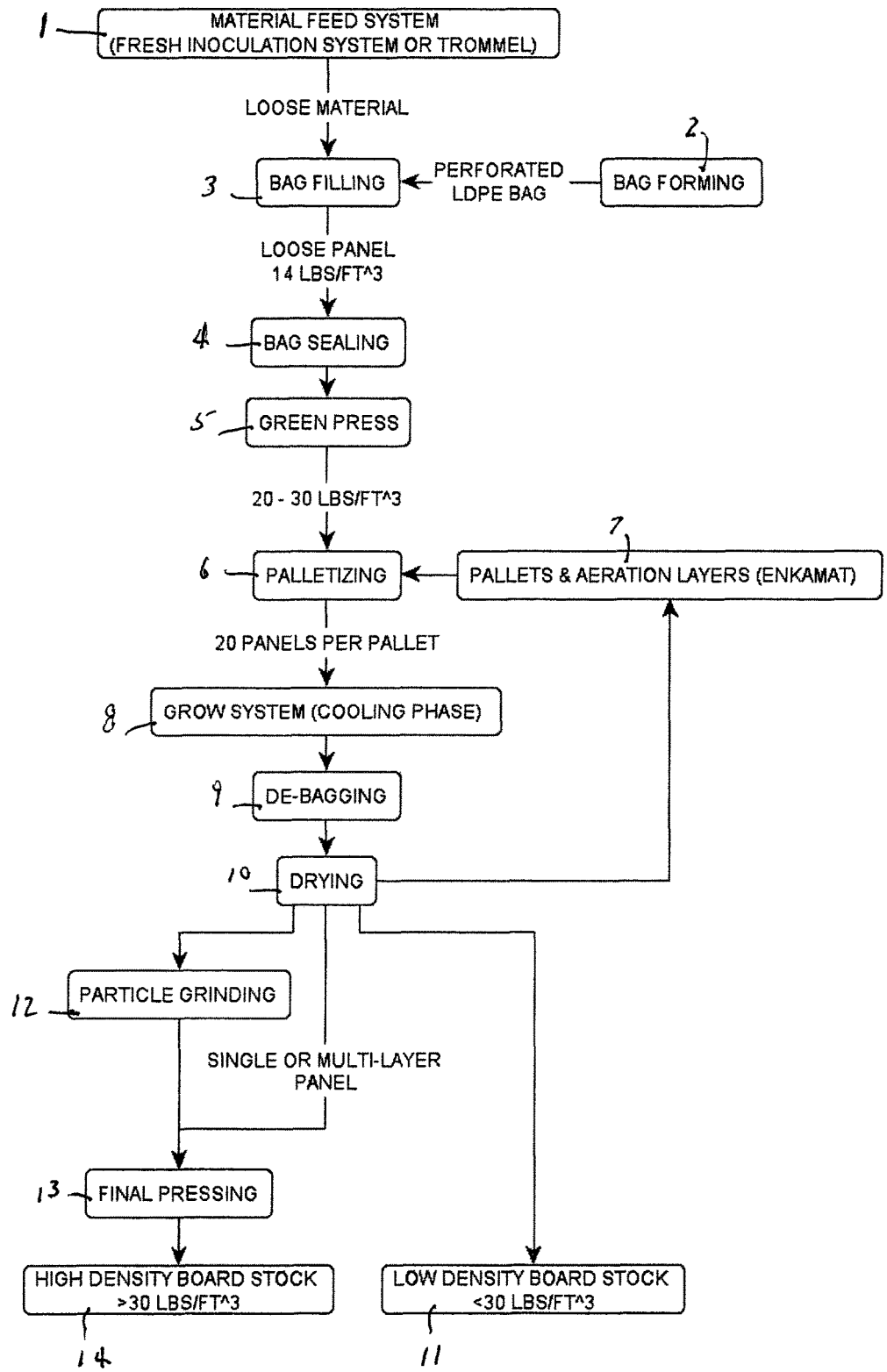

METHOD OF FERMENTING MYCELIUM COMPOSITE MATERIAL

This application claims the benefit of Provisional Patent Application 62/304,448, filed Mar. 7, 2016.

This invention relates to a method of fermenting mycelium composite materials. More particularly, this invention relates to a method of fermenting mycelium composite materials employing a horizontal solid state reactor.

As is known, U.S. Pat. No. 9,485,917 describes several techniques for producing mycelium composite materials. Several of these techniques employ a step of incubating, i.e. fermenting, a substrate containing discrete particles that has been inoculated with a fungus over a period of time sufficient for the fungus to digest nutrient material within the substrate and to grow hyphae that form a network of interconnected mycelia cells to bind the discrete particles together to form a self-supporting composite material.

As is known, aerobic fermentation processes generate heat and carbon dioxide, while consuming oxygen. Also, as is known, an aerobic fermentation process is not a naturally self-optimizing process—meaning that the generation of heat and carbon dioxide when not properly managed can quickly build to levels which limit the rate of fermentation. Therefore, in fermentation processes, it is necessary to control heat and gas buildup to achieve desirable results.

At the lab scale, the quantity of material is often small enough that a tray or bag will diffuse its heat and gas buildup to the environment sufficiently. As systems are scaled to industrial sizes, many small trays or bags become impractical, along with the costly infrastructure to hold each bag or tray sufficiently separated for ventilation. Growth in a single large vessel is restricted by the rate of heat transfer from the center of the pile to the edges, as well of the rate of gas exchange from the center to the edges. In practice, this has been found to limit a single tray or bag to no more than 8 inches of depth in its thinnest dimension.

One solution is to force a fluid (air typically) through a volume of fermenting material in order to remove heat and gas build up. However, in species of fungus which produce significant vegetative tissue and thereby restrict the airflow, the power required to force aeration can quickly make this option economically unfeasible. Additionally, aerating through the fermenting material directly introduces new contamination and desiccation risks.

A second solution is to periodically agitate the fermenting material. This allows greater heat removal and gas exchange from the center of a volume. Unfortunately, it also disrupts the growth of any cohesive mycelial structure, and has also been shown to slow growth in some cases. When the objective is a cohesive final product, agitation is counter productive.

Accordingly, it is an object of the invention to simplify the fermentation step for producing mycelium composite materials.

It is another object of the invention to provide a low cost technique for producing mycelium composite materials.

It is another object of the invention to produce cohesive flat boards of solid-state fermented material, such as are used in the manufacture of insulation or furniture.

Briefly, the invention provides a method of fermenting mycelium composite materials wherein layers of fermentable material are stacked in alteration with ventilation layers with air being passed through the ventilation layers to remove heat and gas generated in the layers of fermentable material during fermentation thereof.

In accordance with the invention, the layers of fermentable material are within an enclosed volume provided, for example, by a bag, which has as a thickness of, at most, the maximum depth that can sufficiently diffuse harmful gas and temperature build up from the center.

The barrier of the enclosed volume is a low cost disposable membrane with desirable properties of gas exchange, vapor transmission, and thermal transmission for regulating the interior atmosphere and preventing contamination. The enclosed volume might also be a reusable membrane, such as a conveyor belt which would be a conveyor belt on the top and bottom face such that the gas exchange permeates through the two open faces (e.g. the sides).

The ventilation layers allow air to be drawn through to remove heat and gas build up. The ventilation layers are formed of a highly porous but incompressible flow media, such as sold under the name EnkaMat. Enkamat is a dense three-dimensional permanent turf reinforcement mat, made of thick polyamide filaments fused where they cross.

The stacking arrangement eliminates the need to use racking to keep growing volumes separated as the weight of each bag is supported by the stack of bags below.

In some cases, the bags of loose material can be slightly compressed in order to provide a more stable and higher mass/floor space efficiency stack.

Additional savings versus bags on racks are found because the length of the bag in the direction perpendicular to the ventilation flow is irrelevant. In this way, it is possible to have very large volumes of material in a single bag while still effectively controlling heat and gas buildup. Embodiments are also possible which operate continuously in this axis, with freshly inoculated material being introduced into a moving layer which is ventilated until grown and then discharged in a continuous process.

Using this innovation allows an increase the amount of fermenting material per volume of warehouse space by five times compared with a rack based bag or tray grow system. Additionally, where the grow volumes are in the shape of a final board, this system has been found an effective means of producing cohesive flat boards of solid-state fermented material, such as are used in the manufacture of insulation or furniture.

These and other objects and advantages of the invention will become more apparent from the following detailed description taken in conjunction with the accompanying drawing wherein:

The Drawing illustrates a flow chart of the method of the invention.

Referring to the Drawing, the method of fermenting mycelium composite materials includes an initial step of obtaining a fermentable material, such as described in U.S. Pat. No. 9,485,917, containing discrete particles and nutrient and inoculated with a fungus capable of forming a network of interconnected mycelia cells to bind the discrete particles together to form a self-supporting composite material upon aerobic fermentation thereof.

The material may be obtained from a material feed system 1 based on a fresh inoculation system or a trammel (a rotating cylindrical sieve or screen) and delivered as a loose material.

Next, the method includes the step of enclosing a volume of the fermentable material in each of a plurality of elongated enclosures with each enclosure characterized in being permeable to gas and vapor for aerobic fermentation of said fermentable material.

In this regard, use may be made of a bag forming station 2 to provide a supply of perforated low density polyethylene (LDPE) bags to a bag filling station 3 wherein the delivered loose material is filled into the bags. Typically, the bags provide an elongated panel shape and the density of the material in the bags is 14 pounds per cubic foot.

The filled bags are then sealed in a bag sealing station 4 and passed through a pressing station 5 to obtain a "green" press wherein the density of the material in the bags is increased to 20 to 30 pounds per cubic foot.

In addition, the method includes the step of obtaining a plurality of ventilation (aeration) layers from a supply station 7, each layer characterized in being porous to the passage of air.

Next, the method includes the step of stacking a plurality of enclosures (elongated bags) and a plurality of ventilation layers vertically in alternating manner to form a stack in a palletizing station 6. For example, a stack is formed of 20 panels (elongated bags) per pallet.

Thereafter, each stack (or pallet) is delivered to a grow system station 8 with a cooling phase.

During the time in the grow system station 8, the fungus in the bags grows in an aerobic fermentation manner to form a network of interconnected mycelia cells to bind the discrete particles together to form a self-supporting composite material.

At the same time, air is passed through the ventilation layers of the stack to remove heat and gas generated in the bags (enclosures) of the stack during fermentation thereof. This step of passing air through the ventilation layers is maintained until formation of a self-supporting composite material is obtained in each bag (enclosure) in the stack.

Next, the method includes the steps of moving a stack from the grow system station 8 to a de-bagging station 9 wherein a self-supporting composite material is removed from each bag of a stack and then subsequently dried in a drying station 10 to a density of less than 30 pounds per cubic foot resulting in a low density board stock 11.

Typically, each said self-supporting composite material is of rectangular board shape.

After drying, a self-supporting composite material may be ground in a particle grinding station 12 into particles and then delivered to a final pressing station 13 to form an element, such as a high density board stock 14 having a density of greater than 30 pounds per cubic foot.

Alternatively, after drying in the drying station 10, a plurality of bags (enclosures) may be stacked to form a multi-layer panel and then pressed in the final pressing station 13 to a density greater than 30 pounds per cubic foot.

Also, after drying in the drying station, a self-supporting composite material may be recycled to the supply station 7 for the ventilation layers for re-stacking.

The invention thus simplifies the fermentation step for producing mycelium composite materials while providing a low cost technique for producing mycelium composite materials and particularly cohesive flat boards of solid-state fermented material, such as are used in the manufacture of insulation or furniture.

What is claimed is:

1. A method of fermenting mycelium composite materials comprising the steps of
    obtaining a fermentable material containing discrete particles and nutrient and inoculated with a fungus capable of forming a network of interconnected mycelia cells to bind the discrete particles together to form a self-supporting composite material upon aerobic fermentation thereof;
    enclosing a volume of said fermentable material in each of a plurality of elongated enclosures, each said enclosure characterized in being permeable to gas and vapor for aerobic fermentation of said fermentable material;
    obtaining a plurality of ventilation layers, each said ventilation layer characterized in being porous to the passage of air;
    stacking said plurality of enclosures and said plurality of ventilation layers vertically in alternating manner to form a stack; and
    passing air through said ventilation layers of said stack to remove heat and gas generated in said enclosures of said stack during fermentation thereof.

2. A method as set forth in claim 1 further comprising the step of pressing each said enclosure prior to said step of stacking to compress said fermentable material to a density of from 20 to 30 pounds per cubic foot.

3. A method as set forth in claim 1 further comprising the step of maintaining the step of passing air through said ventilation layers until formation of a self-supporting composite material is obtained in each said enclosure of said plurality of enclosures.

4. A method as set forth in claim 3 further comprising the steps of removing a self-supporting composite material from each said enclosure of said plurality of enclosures and subsequently drying each said self-supporting composite material to a density of less than 30 pounds per cubic foot.

5. A method as set forth in claim 4 wherein each said self-supporting composite material is of rectangular board shape.

6. A method as set forth in claim 3 further comprising the steps of removing a self-supporting composite material from at least one enclosure of said plurality of enclosures and subsequently grinding the removed self-supporting composite material into particles.

7. A method as set forth in claim 6 further comprising the step of pressing said particles to form an element having a density of greater than 30 pounds per cubic foot.

8. A method as set forth in claim 3 further comprising the steps of removing a self-supporting composite material from each said enclosure of said plurality of enclosures, subsequently stacking a plurality of removed self-supporting composite material to form a multi-layer panel and pressing said panel to a density greater than 30 pounds per cubic foot.

9. A method of fermenting mycelium composite materials comprising the steps of
    obtaining a fermentable material containing discrete particles and nutrient and inoculated with a fungus capable of forming a network of interconnected mycelia cells to bind the discrete particles together to form a self-supporting composite material upon aerobic fermentation thereof;
    enclosing a volume of said fermentable material in each of a plurality of enclosures, each said enclosure characterized in being permeable to gas and vapor for aerobic fermentation of said fermentable material;
    obtaining a plurality of ventilation layers, each said ventilation layer characterized in being porous to the passage of air;
    stacking said plurality of enclosures and said plurality of ventilation layers vertically in alternating manner to form a stack;
    thereafter allowing said fungus in each said enclosure to grow in an aerobic fermentation manner to form a network of interconnected mycelia cells to bind the discrete particles therein together to form a self-supporting composite material; and passing air through said ventilation layers of said stack to remove heat and gas generated in said enclosures of said stack during fermentation thereof.

10. A method as set forth in claim 9 further comprising the steps of subsequently removing each said enclosure containing a self-supporting composite material from said stack, drying each enclosure removed from said stack, thereafter stacking a plurality of said dried enclosures to form a multi-layer panel and then pressing said panel to a density of greater than 30 pounds per cubic foot.

11. A method as set forth in claim 9 further comprising the steps of removing a self-supporting composite material from each said enclosure of said plurality of enclosures and subsequently drying each said self-supporting composite material.

* * * * *